(12) United States Patent
Vandewalle et al.

(10) Patent No.: US 6,190,392 B1
(45) Date of Patent: Feb. 20, 2001

(54) METHOD AND APPARATUS FOR ULTRASONIC REMOVAL OF BONE CEMENT MATERIAL

(75) Inventors: Mark V. Vandewalle, Pierceton; Dean R. Golden, Warsaw, both of IN (US)

(73) Assignee: Biomet, Inc., Warsaw, IN (US)

( * ) Notice: Under 35 U.S.C. 154(b), the term of this patent shall be extended for 0 days.

(21) Appl. No.: 09/497,046

(22) Filed: Feb. 2, 2000

Related U.S. Application Data
(60) Provisional application No. 60/118,454, filed on Feb. 3, 1999.

(51) Int. Cl.$^7$ .......................................................... A61F 2/00
(52) U.S. Cl. ................................................. 606/99; 606/86
(58) Field of Search ................................. 606/1, 53, 79, 606/80, 86, 99

(56) References Cited

U.S. PATENT DOCUMENTS

| | | |
|---|---|---|
| D. 339,419 | 9/1993 | Hood et al. . |
| D. 340,871 | 11/1993 | Iwamura . |
| D. 341,201 | 11/1993 | Hood et al. . |
| D. 341,202 | 11/1993 | Hood et al. . |
| D. 342,313 | 12/1993 | Hood et al. . |
| D. 345,794 | 4/1994 | Hood et al. . |
| 4,248,232 | 2/1981 | Engelbrecht et al. . |
| 5,019,083 | 5/1991 | Klapper et al. . |
| 5,045,054 | 9/1991 | Hood et al. . |
| 5,151,099 | 9/1992 | Young et al. . |
| 5,318,570 | 6/1994 | Hood et al. . |
| 5,358,505 | * 10/1994 | Wuchinich ............................... 606/99 |
| 5,382,251 | * 1/1995 | Hood et al. .............................. 606/99 |
| 6,068,632 | * 5/2000 | Carchidi et al. ........................ 606/79 |

OTHER PUBLICATIONS

Ultra–Drive 50 Operators Manual, AOT, Inc., Rev. P3, May 1993.
Ultra–Drive brochure, copyright, 1993, Biomet, Inc. 6 sheets.
Sonokinetics, Inc., Acryl–X™ Orthopedic Cement Removal System, Rivision Arthroplasty; Copyright 1995, Medical Internet Communications, 2 sheets.
Sodem Ultrasonic System Cemented Implant Revision, 2 sheets. (no date).
Oscar Orthosonics System for Cemented Arthroplasty Revision Technical Brochure, 10 sheets. (no date).

* cited by examiner

Primary Examiner—Jeffrey A. Smith
(74) Attorney, Agent, or Firm—Harness, Dickey & Pierce, P.L.C.

(57) ABSTRACT

A method and apparatus for ultrasonic removal of bone cement material includes an auger tool and an ultrasonic transducer/hand piece. The auger tool includes a spiral helical flute which extends about a cylindrical body and a quick connect mechanism for coupling the auger tool to the ultrasonic transducer/hand piece. Upon energizing the hand piece, bone cement is heated to a flowing mass so that the flowing mass of bone cement may flow about the cylindrical body and guided, via the spiral helical flute 90. This provides a method and apparatus for easily and quickly removing bone cement material during a revision type orthopedic surgical procedure.

19 Claims, 2 Drawing Sheets

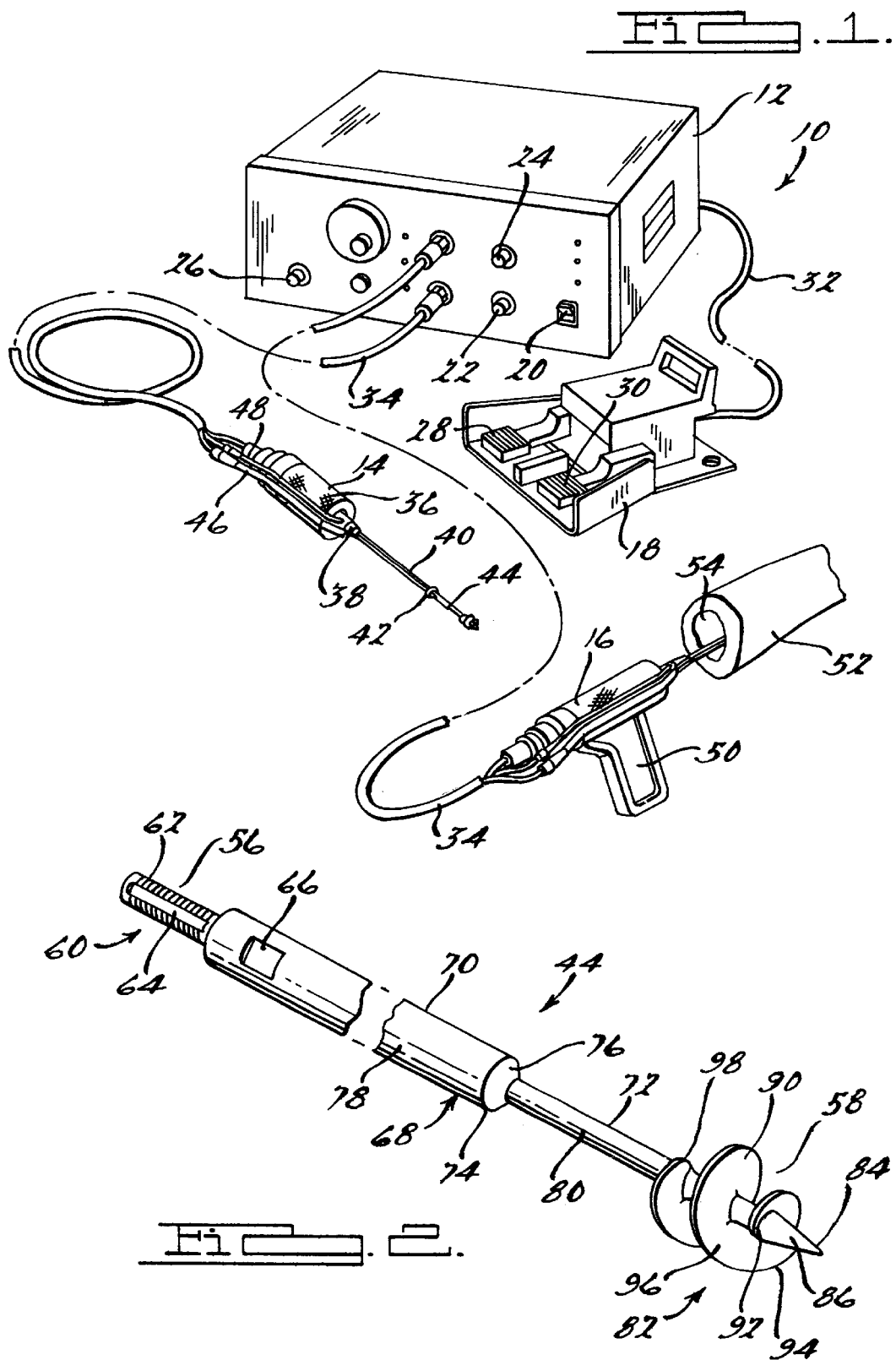

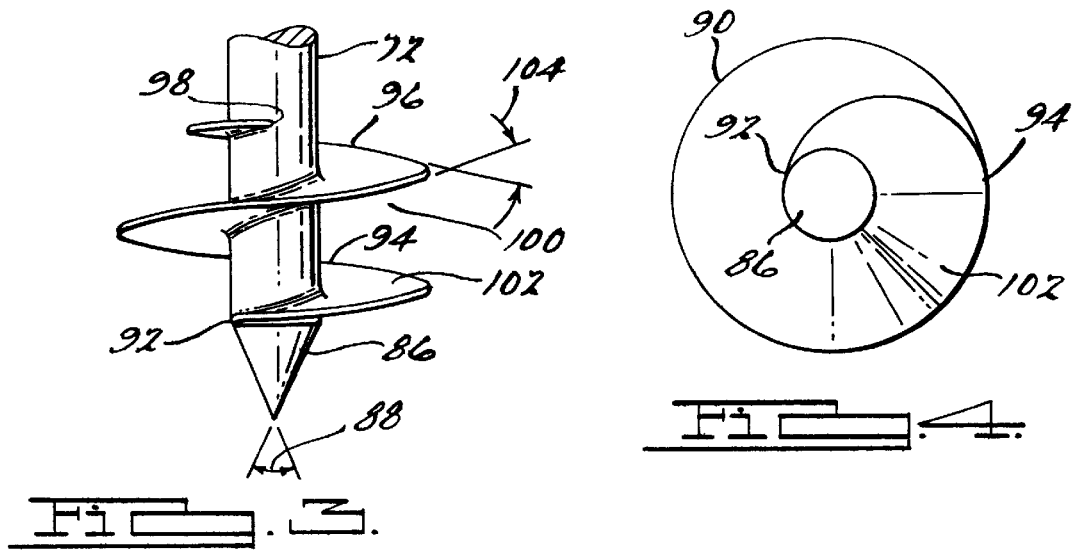
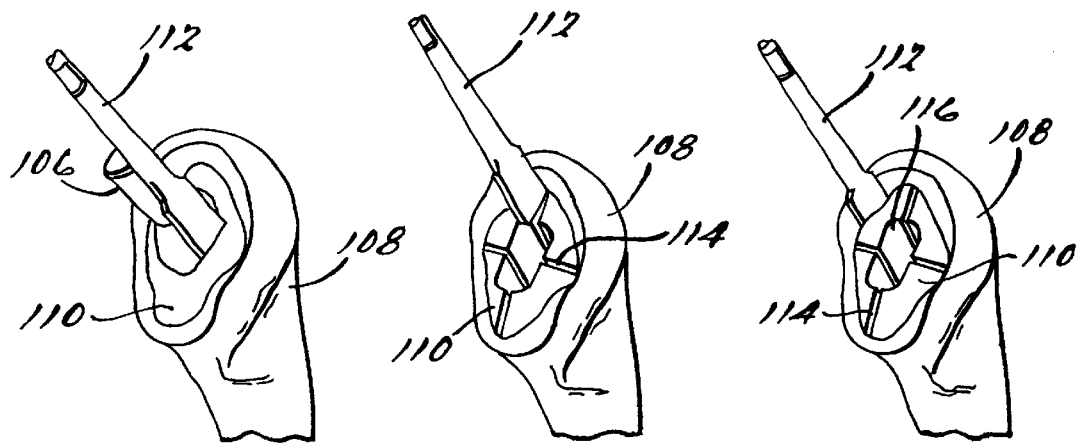
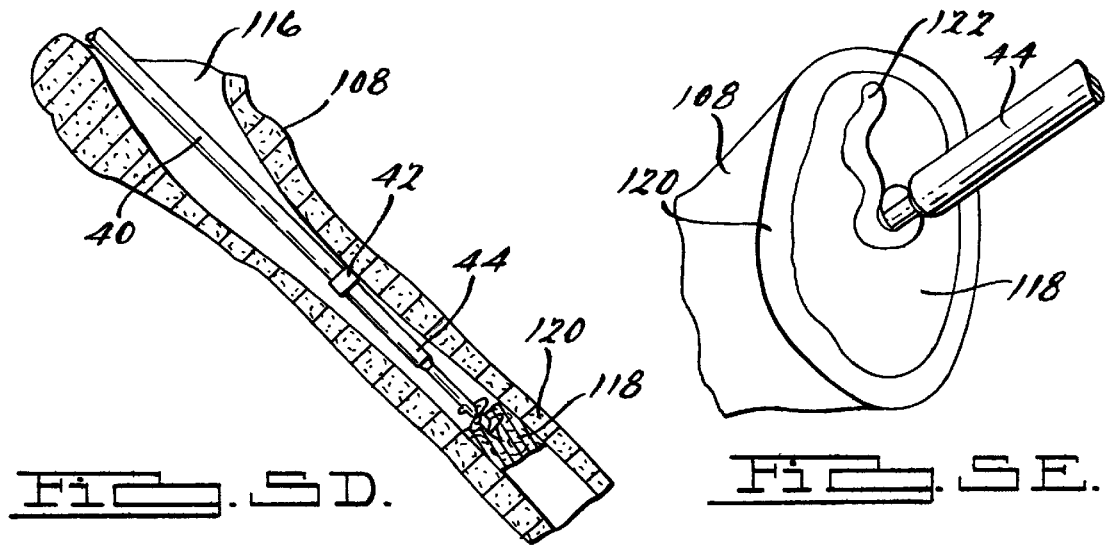

METHOD AND APPARATUS FOR ULTRASONIC REMOVAL OF BONE CEMENT MATERIAL

CROSS-REFERENCE TO RELATED APPLICATIONS

This application claims priority to provisional Application No. 60/118,454 filed on Feb. 3, 1999 and entitled "Method and Apparatus for Ultrasonic Removal of Bone Cement Material."

BACKGROUND OF THE INVENTION

1. Field of the Invention

This invention relates generally to a method and apparatus for use in orthopedic surgery, and more particularly, to a method and apparatus for ultrasonic removal of bone cement material during an orthopedic surgical procedure.

2. Discussion of the Related Art

A natural joint may undergo degenerative changes due to a variety of etiologies. When these degenerative changes become so far advanced and irreversible, it may ultimately become necessary to replace the natural joint with a joint prosthesis. Such joint prostheses include, for example, shoulder, knee and hip joint prostheses. These different prosthetic devices are generally secured by means of bone cement, such as polymethylmethacrylate (PMMA). However, due to any number of reasons, some of the implanted prostheses may require subsequent removal and implantation of a new prosthesis during what is generally referred to as a revision type surgery. As the number of prosthetic implants increases, a corresponding number of revision arthroplasties will also increase.

One of the main challenges facing a surgeon during a revision procedure is the arduous task of complete prosthesis/cement removal. There are various techniques used to remove the prosthesis and bone cement during revision surgery, however, these techniques exhibit disadvantages. For example, manual instruments, such as osteotomes do not offer the surgeon the tactile feedback that aids in distinguishing between the bone cement and the actual bone. High speed burrs or drills have shortened the time required for removal of the bone cement versus the manual instruments. Unfortunately, these types of instruments also lack the tactile feedback which may lead to inadvertent removal or perforation of the patient's cortical bone.

Other techniques used to remove bone cement include the use of ultrasonic mechanical energy. In this regard, electrical energy is converted into mechanical energy, via an ultrasonic transducer. This mechanical energy, in turn, is transmitted through individually tuned tool tips in acoustic waves, causing the tips to vibrate at very high, yet controlled rates of speed. This action breaks down the bone cement in three ways. First, softening by intermolecular friction as the tool tip moves within the cement mantle. Second, by cavitation as the molecular structure begins to rapidly accelerate. Finally, by providing mechanical separation of the cement through cutting, via the tool tip itself. This ultrasonic technique reduces or eliminates some of the previous disadvantages associated with earlier cement removal techniques. However, the ultrasonic technique may further be improved upon.

What is needed then is a method and apparatus for ultrasonic removal of bone cement material which does not suffer from the above mentioned disadvantages and improves upon existing technology. This, in turn, will reduce the incidence of perforation of the cortical bone, reduce the cement removal time, reduce the overall surgical time and therefore, surgical cost, and provide a means for easily removing bone cement which provides a high degree of tactile feedback during the overall surgical procedure. It is, therefore, an object of the present invention to provide such a method and apparatus for ultrasonic removal of bone cement material during an orthopedic surgical procedure.

SUMMARY OF THE INVENTION

In accordance with the teachings of the present invention, a method and apparatus for ultrasonic removal of bone cement material during an orthopedic surgical procedure is disclosed. In this regard, an ultrasonically tuned tool tip having a helical flute is used to easily guide and remove bone cement during a revision type orthopedic surgical procedure. An ultrasonic hand piece is coupled to the tool to impart ultrasonic mechanical energy to the tip of the tool.

In one preferred embodiment, an ultrasonic tool for use in removal of bone cement material includes a connector portion, a shaft and an auger head. The connector portion is operable to be connected to an ultrasonic apparatus. The shaft extends from the connector portion. The auger head is coupled to the shaft and includes a conical tip and a helical flute. The helical flute defines a helical channel that extends along at least a portion of the shaft and is operable to pass bone cement material.

In another preferred embodiment, an ultrasonic system for use in removal of bone cement material includes an ultrasonic power console, an ultrasonic transducer hand piece and an ultrasonic tool. The ultrasonic transducer hand piece is driven by the ultrasonic power console. The ultrasonic tool is coupled to the ultrasonic transducer hand piece and includes an auger head having a conical tip and a helical flute. The helical flute defines a helical channel that is operable to pass bone cement material upon driving the ultrasonic transducer hand piece with the ultrasonic power console.

In yet another preferred embodiment, a method for ultrasonic removal of bone cement material is disclosed. This method includes providing a first ultrasonic tool having a first auger head that includes a first conical tip and a first helical flute that defines a first helical channel. Ultrasonic power is supplied to the first ultrasonic tool to cause the first auger head to vibrate. The first ultrasonic tool is guided with the first conical tip into the bone cement material to guide molten bone cement material along the first helical channel.

Use of the present invention provides an improved method and apparatus for ultrasonic removal of bone cement material during an orthopedic surgical procedure. As a result, the aforementioned disadvantages associated with the currently available methods and techniques for removing bone cement during orthopedic surgical procedures have been substantially reduced or eliminated.

BRIEF DESCRIPTION OF THE DRAWINGS

Still other advantages of the present invention will become apparent to those skilled in the art after reading the following specification and by reference to the drawings in which:

FIG. 1 is a perspective view of an apparatus for ultrasonic removal of bone cement material according to the teachings of the present invention;

FIG. 2 is a perspective view of an ultrasonically tuned tool tip according to the teachings of the present invention;

FIG. 3 is a side elevational view of the ultrasonic tool tip of FIG. 1;

FIG. 4 is an end view of the ultrasonic tool tip of FIG. 1; and

FIGS. 5A–5E illustrate a method for ultrasonic removal of bone cement material according to the teachings of the present invention.

DETAILED DESCRIPTION OF THE PREFERRED EMBODIMENT(S)

The following description of the preferred embodiment concerning a method and apparatus for ultrasonic removal of bone cement material is merely exemplary in nature and is not intended to limit the invention or its application or uses. Moreover, while the present invention is described in detail below with reference to a specific ultrasonic system for removing bone cement during a revision type surgery on a femoral hip, it will be appreciated by those skilled in the art that the present invention is clearly not limited to the specific ultrasonic system disclosed herein or for the removal of bone cement only during hip revision surgery, but may be used with any type of ultrasonic system and applied to other prosthetic devices which are implanted by way of bone cement, such as shoulder and knee prosthetic devices.

Referring to FIG. 1, an apparatus 10 for ultrasonic removal of bone cement material is shown. The apparatus 10 is preferably the Ultra-Drive® System offered by Biomet, Inc. of Warsaw, Ind. A detailed description of the workings of the Ultra-Drive apparatus 10 is set forth in U.S. Pat. Nos. 4,248,232, 5,019,083, 5,045,054 and 5,318,570, which are hereby incorporated by reference. In general, the apparatus 10 includes an ultrasonic power unit or console 12 which drives a first hand piece 14 and a second hand piece 16, via a foot pedal control unit 18.

The console 12, in general, includes an on/off switch 20 for turning the console on, a hand piece select knob 22 for selecting either the hand piece 14 or 16, a power selection knob 24 for selecting the percent power applied to either hand piece 14 or 16, and a flow control knob 26 to control the amount of irrigation fluid supplied to the surgical site, further discussed herein. The foot pedal control unit 18 includes a first foot pedal 28 and a second foot pedal 30. Actuation of the first foot pedal 28 directs the console 12, via control line 32, to provide only irrigation fluid to the surgical site. Actuation of the second foot pedal 30 directs the console, via control line 32, to provide both irrigation fluid, as well as power to either of the hand pieces 14 or 16.

Each transducer/hand piece 14 or 16 is controlled by the ultrasonic power unit or console 12, via individual control lines 34. The hand piece 14 includes a knurled handle 36 housing an ultrasonic transducer and a quick connect chuck 38. Coupled to the quick connect chuck 38 is a quick connect extender 40, also containing a quick connect chuck 42. The optional quick connect extender 40 is used in various orthopedic surgical procedures where increased length is required to guide an ultrasonic tool 44 of the present invention to the surgical site. The ultrasonic tool 44, further discussed herein, is used generally for removing bone cement from a bone cement plug within a femur. However, other uses of the ultrasonic tool 44 is also contemplated. In addition to the ultrasonic tool 44 of the present invention, other types of ultrasonic tools may also be coupled to either the quick connect extender 40 or to the hand piece 14 directly depending on the surgical application. These ultrasonic tools include various shaped osteotomes, hoes, gouges, disk drills and plug pullers, all available from Biomet, Inc. and some of which are set forth in U.S. Pat. Nos. D340,981, D341,201, D341, 202, D339,419 and D342, 313, all of which are hereby incorporated by reference.

Extending axially from the hand piece 14 is a first irrigation tube 46 and a second fiberoptic tube 48. The first irrigation tube 46 provides irrigation fluid to the surgical site where ultrasonic removal of the bone cement occurs. The second fiberoptic tube 48 provides illumination intraoperatively should a further light source be desired. Both tubes 46 and 48 are supplied, and in communication with the ultrasonic power unit or console 12, via the control line 34. An optional piston grip 50 may also be removably coupled to the knurled handle 38 should better handling be desired. While the hand piece 14 has been described in detail above, it should be recognized that the hand piece 16 is configured substantially the same as the hand piece 14. In this regard, the two hand pieces 14 and 16 are provided to offer the surgeon the opportunity to switch between two different ultrasonic tools by simply selecting one of the hand pieces 14 or 16 and turning the hand piece select knob 22. In this way, a surgeon can quickly and readily switch between two different types of ultrasonic tools without having to remove a tool from a hand piece. As shown in FIG. 1, the hand piece 14 is shown in operative proximity to a femur 52 for use in removal of bone cement 54.

Turning to FIGS. 2–4, the improved ultrasonic tool 44 according to the teachings of the present invention is shown in further detail. The ultrasonic tool 44 is preferably formed from titanium or other appropriate biocompatible material. The ultrasonic tool 44 includes a proximal end 56 and a distal end 58. The proximal end 56 includes a quick connect portion 60 having opposed threaded sidewalls 62 and opposed planar sidewalls 64. In this regard, the tool 44 is simply slid into a quick connect receiving bore of the quick connect chuck 42 in the extender 40 or the quick connect chuck 38 of the hand piece 14 and rotated 90 degrees (90°), thereby threadably locking the threads 64 with mating threads in the quick connect chuck 42 or 38. A further detailed description of this quick connect mechanism is set forth in U.S. Pat. No. 5,318,570, which is hereby incorporated by reference. In order to lock and unlock the tool 44 from the quick connect chuck 42 or 38, a pair of opposed notches 66 are provided which may be engaged by a wrench.

The body 68 of the tool 44 is comprised of a first elongated cylindrical portion 70 having a first diameter and a second elongated cylindrical portion 72 having a second smaller diameter. A conical transition portion 74 having a conical sidewall 76 extends between a cylindrical sidewall 78 of the cylindrical portion 70 and a cylindrical sidewall 80 of the cylindrical portion 72.

Positioned at the distal end 58 of the tool 44 is an auger head 82. The auger head 82 includes a conical tip 84 formed from a conical sidewall 86 having an angle 88 of sixty degrees (60°). Extending from the conical sidewall 86 is a single helical flute 90 that originates from the conical sidewall 86. The single helical flute 90 of the auger 82 originates at point 92 (i.e., 0°) and the radius increases up to point 94 or at about 180° of rotation about the cylindrical shaft portion 72. From point 94 to point 96, or at about 180° of rotation to about 540° of rotation, the radius of the helical flute 90 is substantially constant. From point 96 to point 98, the radius of the flute 90 decreases between about 540° to about 720° of rotation about the cylindrical portion 72. The single helical flute 90 has a shallow helical angle of between about nine degrees (9°) to about fourteen degrees (14°) that provides for a compact auger head 82.

The spiral transition regions between point 92 to point 94 and between point 96 to point 98 enables the melted and flowing bone cement to be drawn up along a channel 100 defined by the helical flute 90. The helical flute 90 also includes sidewalls 102 which angle at about eight degrees (8°) individually, relative to the axis of the tool 44, identified by reference numeral 104, or sixteen degrees (16°) inclusive. This shallow angle provides a sufficiently large channel 100 to guide a sufficient amount of flowing bone cement spiraling along the flute 90. The shallow angle 104 further reduces the mass of the auger head 82 to provide increased vibration and oscillation at the auger head 82. In addition, the single helical flute 90 is easy to manufacture and provides better performance than a double or triple flute device.

Turning now to FIGS. 5A–5E, a method for ultrasonic removal of bone cement material utilizing the ultrasonic apparatus 10 and the ultrasonic tool 44 according to the teachings of the present invention will be discussed. In this regard, it should again be noted that while the ultrasonic removal of bone cement disclosed herein is directed to removal of a femoral component implanted within a femur, it will be understood by those skilled in the art that this method is merely exemplary and may be equally applied to the removal of various other prosthetic devices and/or cement from other areas.

Referring to FIG. 5A, a femoral component 106 is shown implanted in a femur 108 by way of a hardened cement mantle 110. In order to remove the femoral component 106, an osteotome ultrasonic tool 112 is employed. In this regard, the power switch 20 is turned on, the hand piece select switch is adjusted to actuate the hand piece in use, the irrigation flow control knob 26 is adjusted, and the power control knob 24 is set to between about fifty percent (50%) to seventy percent (70%) on the ultrasonic power console 12. The osteotome 112 is then located between the femoral component 106 and the cement mantle 110. Once in position, the second foot pedal 30 is activated to irrigate and provide ultrasonic power to the hand piece 14 or 16 in use. A constant up and down motion is used to guide the osteotome 112, along the anterior and posterior planes of the femoral component 106 while the irrigation fluid is used to ensure that the osteotome 112 does not become sealed or stuck in the cement mantle 110. A first straight osteotome 112 may be used along the anterior and posterior planes of the femoral component 106, while a curved osteotome may be used along the medial and lateral interface of the femoral component 106. Upon guiding the osteotome 112 into the cement mantle 110, substantially about the periphery of the femoral component 106, the femoral component 106 may be removed from within the femur 108.

Once the femoral component 106 is removed from the femur 108, the straight osteotome 112 is used to form multiple troughs 114 extending axially into the intramedullary canal 116 of the femur 108, as shown in FIG. 5B. The troughs 114 are positioned at 12, 3, 6 and 9 o'clock relative to the femur 108. To cut the troughs 114, the surgeon should proceed distally with the osteotome 112 using a side-to-side oscillating motion to widen the troughs. This same motion should also be used while drawing the osteotome proximally. Here again, it is important to maintain constant irrigation, as well as the back and forth motion to ensure that the osteotome is not sealed into the cement mantle 110.

Once the troughs 114 are formed, the cement mantle 110 should be removed by guiding the osteotome 112 between the cement mantle 110 and the femur 108, as shown in FIG. 5C. The osteotome 112 should be guided again using irrigation and a back and forth motion along the cement/bone interface to allow the introduction of saline between the femur 108 and the cement mantle 110. Once the initial path between the femur 108 and the bone cement mantle 110 has been created with the osteotome 112, a manual osteotome positioned between the bone 108 and the cement mantle 110 can be used to gently loosen large sections of the cement mantle 110. The loosened sections of the cement mantle 110 should be carefully removed from the intramedullary canal 116 with forceps or a rongeur.

Once the cement mantle 110 has been removed, a bone or cement plug 118 should still be positioned within the intramedullary canal 116 of the femur 108 adjacent to the hard cortical bone 120, as shown in FIG. 5D. The cement plug 118 must generally be converted to a hollow cylinder before its removal from the femur 108. To accomplish this, the auger tool 44 of the present invention will be utilized along with the extender 40 to progressively form a hollow cylinder within the cement plug 118. Using ultrasonic power set to between about 50% and 70% with heavy irrigation, a small diameter auger tool 44 should be introduced through the intramedullary canal 116 of the femur 108. The conical tip 84 acts as a guide mechanism relative to the cement plug 118 to thereby guide the auger tool 44 into the cement plug 118 without contacting the hard cortical wall 120.

As the ultrasonic power is applied to the auger head 82, the auger head 82 vibrates at approximately 40 KHz to heat and cause the cement plug 118 to become molten at its place of contact with the auger head 82. As the cement plug 118 becomes molten in this area, molten cement 122 begins to progressively flow and is guided past the conical sidewall 86 and along the single spiral or helical flute 90 from the conical tip 84 to the point 98 of the auger 82, as shown clearly in FIG. 5E. With the auger tool 44 progressively extending into the bone plug 118, the molten cement 122 is spirally directed along the single channel 100 about the cylindrical portion 72. As the molten cement 122 gathers and flows along the single channel 100 formed by the single flute 90, the molten cement 122 will move about the cylindrical portion 72 starting at point 92 and progressing to points 94, 96 and 98. Slight rotation back and forth assists in moving the molten cement 122 along channel 100. Once the molten cement 122 passes point 98, the auger tool 44 can be removed under ultrasonic power to help evacuate the cement.

Once removed, the excess cement should be wiped off from the auger head 82. The auger head 82 may then be reinserted, with continued cement removal until the cement plug 118 is hollow. Introduction of progressively larger auger tools 44 having larger diameter flutes 90 should continue until the cement plug 118 is reduced to a thickness of about 2–3 millimeters relative to the cortical wall 120.

The sizes of the auger head 82 will generally vary from about 5 millimeters in diameter to about 13 millimeters in diameter relative to the flute 90. Once the thickness of the cement plug 118 is reduced to only about 2–3 millimeters, the remaining portion of the cement plug 118 may be removed using either the osteotome 112 or a manual osteotome. With the cement plug 118 fully removed from the femur 108, the surgeon can then begin to replace the previous femoral component with a new revision femoral component.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An ultrasonic tool for use in removal of bone cement material, said ultrasonic tool comprising:
   a connector portion operable to be connected to an ultrasonic apparatus;
   a shaft extending from said connector portion; and
   an auger head coupled to said shaft, said auger head including a conical tip and a helical flute, said helical flute defining a helical channel that extends along at least a portion of said shaft, said helical channel operable to pass bone cement material.

2. The ultrasonic tool as defined in claim 1 wherein said shaft includes a pair of opposed notches operable to be engaged by a wrench to lock and unlock said ultrasonic tool to the ultrasonic apparatus.

3. The ultrasonic tool as defined in claim 1 wherein a spiral transition region is defined at an origination point of said helical flute to a maximum radius of said helical flute which enables bone cement material to be drawn up along said helical channel.

4. The ultrasonic tool as defined in claim 1 wherein said conical tip includes a conical sidewall and said helical flute originates from said conical sidewall.

5. The ultrasonic tool as defined in claim 4 wherein a radius of said helical flute increases from said origination point at said conical sidewall to about 180° of rotation about said shaft.

6. The ultrasonic tool as defined in claim 5 wherein the radius of said helical flute from 180° to about 540° of rotation about said shaft is substantially constant.

7. The ultrasonic tool as defined in claim 6 wherein the radius of said helical flute from about 540° to about 720° of rotation about said shaft decreases.

8. The ultrasonic tool as defined in claim 1 wherein said shaft is a cylindrical shaft having a first cylindrical portion having a first diameter and a second cylindrical portion having a second diameter with a transition portion therebetween.

9. The ultrasonic tool as defined in claim 1 wherein said helical flute includes helical sidewalls which angle at about 8° relative to a longitudinal axis of said shaft to provide a sufficiently large helical channel to guide a sufficient amount of bone cement material through said helical channel.

10. An ultrasonic system for use in removal of bone cement material, said ultrasonic system comprising:
    an ultrasonic power console;
    an ultrasonic transducer hand piece, said ultrasonic transducer hand piece being driven by said ultrasonic power console; and
    an ultrasonic tool coupled to said ultrasonic transducer hand piece, said ultrasonic tool having an auger head that includes a conical tip and a helical flute, said helical flute defining a helical channel that is operable to pass bone cement material upon driving said ultrasonic transducer hand piece with said ultrasonic power console.

11. The ultrasonic system as defined in claim 10 further comprising a foot petal control unit operable to control said ultrasonic power console.

12. The ultrasonic system as defined in claim 10 wherein said ultrasonic tool further includes a cylindrical shaft and said helical channel extends along at least a portion of said cylindrical shaft.

13. The ultrasonic system as defined in claim 10 wherein said ultrasonic tool further includes a connection portion operable to be connected to said ultrasonic transducer hand piece and a pair of opposed notches operable to be engaged by a wrench to connect and disconnect said ultrasonic tool from said ultrasonic transducer hand piece.

14. The ultrasonic system as defined in claim 10 wherein said ultrasonic tool further includes a spiral transition region extending from said conical tip to along a portion of said helical flute which enables the bone cement material to be drawn up along said helical channel.

15. The ultrasonic system as defined in claim 14 wherein said spiral transition region originates at said conical tip and extends to about 180° of rotation about said cylindrical shaft where a radius of said helical flute increases in said spiral transition region.

16. The ultrasonic system as defined in claim 10 wherein said helical flute includes sidewalls which angle at about 8° relative to a longitudinal axis of said ultrasonic tool to provide a sufficiently large helical channel to guide a sufficient amount of bone cement material along said helical channel.

17. A method for ultrasonic removal of bone cement material, said method comprising:
    providing a first ultrasonic tool having a first auger head that includes a first conical tip and a first helical flute that defines a first helical channel, the first helical flute having a first diameter;
    applying ultrasonic power to the first ultrasonic tool to cause the first auger head to vibrate; and
    guiding the first ultrasonic tool with the first conical tip into the bone cement material to guide molten bone cement material along the first helical channel.

18. A method as defined in claim 17 further comprising:
    providing a second ultrasonic tool having a second auger head that includes a second conical tip and a second helical flute that defines a second helical channel, the second helical flute having a second diameter that is larger than the first diameter;
    applying ultrasonic power to the second ultrasonic tool to cause the second auger head to vibrate; and
    guiding the second ultrasonic tool with the second conical tip into the bone cement material to guide molten bone cement material along the second helical channel.

19. The method as defined in claim 17 further comprising guiding the molten bone cement material along the first helical channel and about a cylindrical shaft in which the first helical flute extends.

* * * * *

UNITED STATES PATENT AND TRADEMARK OFFICE
CERTIFICATE OF CORRECTION

PATENT NO. : 6,190,392 B1  
DATED : February 20, 2001  
INVENTOR(S) : Mark V. Vandewalle and Dean R. Golden It is certified that error appears in the above-identified patent and that said Letters Patent is hereby corrected as shown below:

<u>Column 8,</u>  
Line 2, "petal" should be -- pedal --.

Signed and Sealed this

Twenty-third Day of July, 2002

Attest:

JAMES E. ROGAN  
*Attesting Officer*   *Director of the United States Patent and Trademark Office*